United States Patent
Hamada et al.

(10) Patent No.: US 11,891,505 B2
(45) Date of Patent: Feb. 6, 2024

(54) RESIN COMPOSITION FOR ACOUSTIC MATCHING LAYER, CURED PRODUCT, ACOUSTIC MATCHING SHEET, ACOUSTIC PROBE, ACOUSTIC MEASURING APPARATUS, METHOD FOR PRODUCING ACOUSTIC PROBE, AND ACOUSTIC MATCHING LAYER MATERIAL SET

(71) Applicant: FUJIFILM Corporation, Tokyo (JP)

(72) Inventors: Kazuhiro Hamada, Kanagawa (JP);
Kazushi Furukawa, Kanagawa (JP);
Yoshihiro Nakai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 728 days.

(21) Appl. No.: 16/863,297

(22) Filed: Apr. 30, 2020

(65) Prior Publication Data

US 2020/0270448 A1    Aug. 27, 2020

Related U.S. Application Data

(63) Continuation of application No. PCT/JP2018/040440, filed on Oct. 31, 2018.

(30) Foreign Application Priority Data

Nov. 1, 2017    (JP) .................. 2017-212209

(51) Int. Cl.
| | |
|---|---|
| *C08L 63/00* | (2006.01) |
| *C08K 5/17* | (2006.01) |
| *C08G 59/50* | (2006.01) |
| *G01N 29/24* | (2006.01) |
| *G10K 11/18* | (2006.01) |
| *G10K 11/36* | (2006.01) |
| *C08K 3/08* | (2006.01) |

(52) U.S. Cl.
CPC .......... *C08L 63/00* (2013.01); *C08G 59/5033* (2013.01); *G01N 29/2437* (2013.01); *G10K 11/18* (2013.01); *G10K 11/36* (2013.01); *C08K 5/17* (2013.01); *C08K 2003/085* (2013.01); *C08K 2003/0806* (2013.01); *C08K 2003/0856* (2013.01); *C08K 2003/0862* (2013.01); *C08K 2003/0887* (2013.01); *C08K 2003/0893* (2013.01)

(58) Field of Classification Search
CPC .................. C08L 63/00; C08K 5/17
See application file for complete search history.

(56) References Cited

U.S. PATENT DOCUMENTS

| | | | |
|---|---|---|---|
| 4,485,229 A | 11/1984 | Waddill et al. | |
| 5,891,367 A | 4/1999 | Basheer et al. | |
| 11,242,471 B2 * | 2/2022 | Iseda ........................ | C08K 3/08 |
| 2011/0315916 A1 | 12/2011 | Wilson et al. | |
| 2016/0338666 A1 | 11/2016 | Morita | |

FOREIGN PATENT DOCUMENTS

| | | | |
|---|---|---|---|
| CN | 101173087 A | 5/2008 | |
| CN | 101974303 A | 2/2011 | |
| CN | 102432835 A | 5/2012 | |
| EP | 2 402 395 A2 | 1/2012 | |
| JP | 56-169682 U | 12/1981 | |
| JP | 60-195123 A | 10/1985 | |
| JP | 2009-296055 A | 12/2009 | |
| WO | WO-2015125692 A1 * | 8/2015 | ............. B32B 15/00 |

OTHER PUBLICATIONS

Communication dated Dec. 3, 2020 by the China National Intellectual Property Administration in application No. 201880069785.4.
Communication dated May 28, 2021, issued by the State Intellectual Property Office of the P.R.C. in application No. 201880069785.4.
Extended European Search Report dated Nov. 30, 2020 in European Application No. 18872414.0.
International Search Report dated Jan. 22, 2019 from the International Searching Authority in International Application No. PCT/JP2018/040440.
Written Opinion dated Jan. 22, 2019 from the International Bureau in International Application No. PCT/JP2018/040440.
International Preliminary Report on Patentability dated May 5, 2020 from the International Bureau in International Application No. PCT/JP2018/040440.

* cited by examiner

*Primary Examiner* — Vickey Nerangis
(74) *Attorney, Agent, or Firm* — Sughrue Mion, PLLC

(57) ABSTRACT

Provided is a resin composition for an acoustic matching layer, the resin composition including an epoxy resin (A), a specific polyamine compound (B), and metal particles (C). The epoxy resin (A) includes at least one epoxy resin selected from the group consisting of bisphenol A epoxy resins, bisphenol F epoxy resins, and phenol novolac epoxy resins. Also provided are a cured product formed of the composition, an acoustic matching sheet, an acoustic probe, an acoustic measuring apparatus, a method for producing an acoustic probe, and an acoustic matching layer material set.

11 Claims, 1 Drawing Sheet

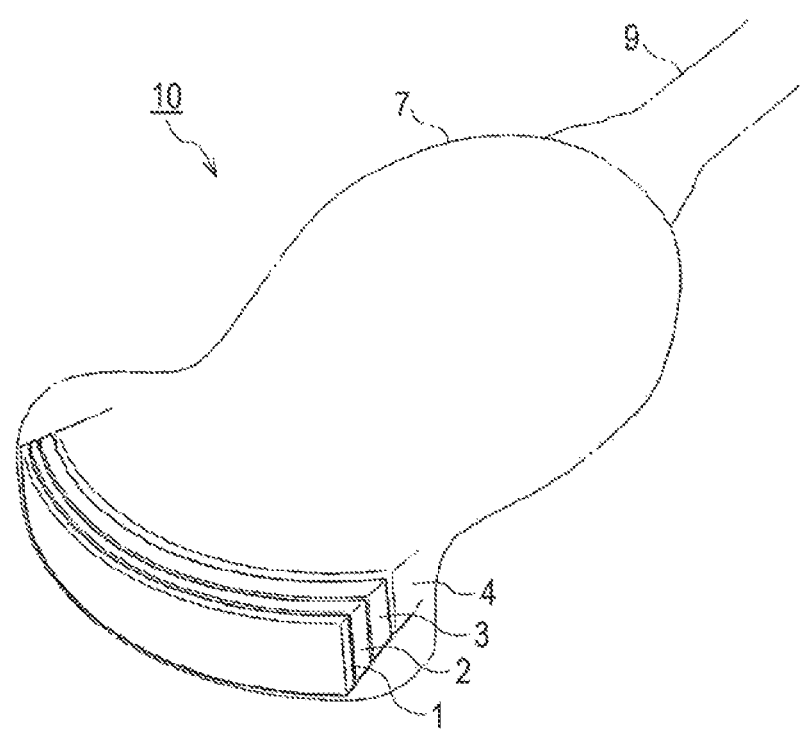

RESIN COMPOSITION FOR ACOUSTIC MATCHING LAYER, CURED PRODUCT, ACOUSTIC MATCHING SHEET, ACOUSTIC PROBE, ACOUSTIC MEASURING APPARATUS, METHOD FOR PRODUCING ACOUSTIC PROBE, AND ACOUSTIC MATCHING LAYER MATERIAL SET

CROSS-REFERENCE TO RELATED APPLICATIONS

This application is a Continuation of PCT International Application No. PCT/JP2018/040440 filed on Oct. 31, 2018, which claims priority under 35 U.S.C. § 119 (a) to Japanese Patent Application No. 2017-212209 filed in Japan on Nov. 1, 2017. Each of the above applications is hereby expressly incorporated by reference, in its entirety, into the present application.

BACKGROUND OF THE INVENTION

1. Field of the Invention

The present invention relates to a resin composition for an acoustic matching layer, a cured product, an acoustic matching sheet, an acoustic probe, an acoustic measuring apparatus, a method for producing an acoustic probe, and an acoustic matching layer material set.

2. Description of the Related Art

An acoustic measuring apparatus includes an acoustic probe that irradiates a subject such as a living body with acoustic waves and receives reflected waves (echoes) therefrom to output a signal. The reflected waves received by the acoustic probe are converted into an electrical signal. The electrical signal is displayed as an image. Therefore, using an acoustic probe allows the inside of a subject to be visualized and observed.

Appropriate acoustic waves such as ultrasonic waves or photoacoustic waves are selected depending on the subject and the measurement conditions.

For example, an ultrasound diagnostic apparatus, which is an acoustic measuring apparatus, transmits ultrasonic waves toward the inside of a subject, receives ultrasonic waves reflected by a tissue inside the subject, and displays an image.

A photoacoustic measuring apparatus receives acoustic waves radiated from inside a subject due to a photoacoustic effect and displays an image. The photoacoustic effect is a phenomenon in which, when a subject is irradiated with pulses of electromagnetic waves such as visible light, near-infrared light, or microwaves, the subject absorbs the electromagnetic waves to cause heat generation and thermal expansion, whereby acoustic waves (typically, ultrasonic waves) are generated.

The acoustic measuring apparatus transmits and receives acoustic waves to and from a subject, and thus the acoustic probe is required to provide acoustic impedance matching to a subject. To meet this requirement, the acoustic probe includes an acoustic matching layer. This will be described with reference to an ultrasound diagnostic apparatus search unit (also referred to as an ultrasound probe), which is an acoustic probe.

The ultrasound probe includes a piezoelectric element for transmitting and receiving ultrasonic waves and an acoustic lens configured to be in contact with a living body, and an acoustic matching layer is disposed between the piezoelectric element and the acoustic lens. Ultrasonic waves oscillated from the piezoelectric element pass through the acoustic matching layer and further through the acoustic lens to enter a living body. In general, there is a difference in acoustic impedance (density×sound velocity) between the acoustic lens and a living body. When this difference is large, ultrasonic waves are likely to be reflected by a living body surface, and the efficiency of entrance of ultrasonic waves into a living body is low. Thus, the acoustic lens is required to have acoustic impedance characteristics close to those of a living body.

On the other hand, the difference in acoustic impedance between the piezoelectric element and a living body is generally large. Accordingly, the difference in acoustic impedance between the piezoelectric element and the acoustic lens is generally large. Therefore, when the piezoelectric element and the acoustic lens are stacked on top of each other, ultrasonic waves emitted from the piezoelectric element are reflected by a surface of the acoustic lens, and the efficiency of entrance of ultrasonic waves into a living body is low. To reduce such reflection of ultrasonic waves, the above acoustic matching layer is disposed between the piezoelectric element and the acoustic lens. The acoustic impedance of the acoustic matching layer is between the acoustic impedance of a living body or the acoustic lens and the acoustic impedance of the piezoelectric element, which increases the efficiency of propagation of ultrasonic waves from the piezoelectric element to a living body. It is also known that when the acoustic matching layer has a multi-layer structure with a gradient in acoustic impedance from the piezoelectric element side toward the acoustic lens side, the efficiency of propagation of ultrasonic waves is further increased.

The acoustic probe is required to have sufficient mechanical strength in addition to the acoustic characteristics described above. The acoustic matching layer is often used in the form of a thin film (e.g., several hundred micrometers), and cutting processing is performed to achieve a desired thickness. Thus, the acoustic matching layer is required to have mechanical strength sufficient to withstand the cutting processing. The acoustic probe is used while being rubbed, sometimes pressed, against a living body, and thus the mechanical strength directly affects the product life of the acoustic probe.

It is known that epoxy resins, polyimide resins, silicone resins, polyolefin resins, cycloolefin resins, polyester resins, polyvinyl butyral resins, and other resins are used as constituent materials of the acoustic matching layer (e.g., JP2009-296055A).

SUMMARY OF THE INVENTION

For the acoustic matching layer of the acoustic probe, a material is employed that has an acoustic impedance adjustable to be at a desired level between an acoustic impedance of the piezoelectric element and an acoustic impedance of a living body. The present inventors have studied and found that the acoustic matching layer disclosed in JP2009-296055A may have poor mechanical strength and variation in intralayer acoustic characteristics.

Thus, an object of the present invention is to provide a resin composition for an acoustic matching layer and an acoustic matching layer material set suitable for preparation of the composition. From the resin composition, an acoustic matching layer having high mechanical strength and little variation in intralayer acoustic characteristics can be formed.

Another object of the present invention is to provide an acoustic matching sheet having high mechanical strength and little variation in intrasheet acoustic characteristics and a cured product used therefor.

Still another object of the present invention is to provide an acoustic probe having high mechanical strength and little variation in acoustic characteristics and an acoustic measuring apparatus including the acoustic probe.

Yet still another object of the present invention is to provide a method for producing an acoustic probe having high mechanical strength and little variation in acoustic characteristics.

To achieve the above objects, the present inventors conducted intensive studies and found that a sheet formed by using a composition for forming an acoustic matching layer, the composition including metal particles, a specific epoxy resin, and a specific polyamine compound serving as a curing agent for the epoxy resin, has high mechanical strength and reduced variation in intralayer acoustic characteristics. The present invention has been completed by further conducting studies based on this finding.

Thus, the above objects of the present invention have been achieved by the following means.

<1> A resin composition for an acoustic matching layer includes an epoxy resin (A), a polyamine compound (B1) represented by general formula (I) below, and metal particles (C).

The epoxy resin (A) includes at least one epoxy resin selected from the group consisting of bisphenol A epoxy resins, bisphenol F epoxy resins, and phenol novolac epoxy resins.

   General formula (I)

In general formula (I), n represents an integer of 2 to 20. L represents an n-valent aliphatic hydrocarbon group having an aliphatic hydrocarbon chain into which at least one oxygen atom is incorporated or an n-valent group having an aromatic ring and an aliphatic hydrocarbon group having at least one oxygen atom.

<2> In the resin composition for an acoustic matching layer according to <1>, the polyamine compound (B1) is at least one polyamine compound represented by general formula (II), (III), or (IV) below.

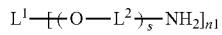   General formula (II)

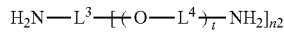   General formula (III)

   General formula (IV)

In general formula (II), s represents an integer of 1 to 100, and n1 represents an integer of 2 to 20. $L^1$ represents an n1-valent aliphatic hydrocarbon group having 1 to 20 carbon atoms or an n1-valent aromatic hydrocarbon group having 6 to 20 carbon atoms, and $L^2$ represents an aliphatic hydrocarbon chain having 2 to 6 carbon atoms.

In general formula (III), t represents an integer of 1 to 100, and n2 represents an integer of 1 to 19. $L^3$ represents an (n2+1)-valent aliphatic hydrocarbon group having 1 to 20 carbon atoms or an (n2+1)-valent aromatic hydrocarbon group having 6 to 20 carbon atoms, and $L^4$ represents an aliphatic hydrocarbon chain having 2 to 6 carbon atoms.

In general formula (IV), u represents an integer of 1 to 100, n3 and n4 each represent an integer of 1 or more, and the sum of n3 and n4 is 20 or less. $L^5$ represents an (n3+1)-valent aliphatic hydrocarbon group having 1 to 20 carbon atoms or an (n3+1)-valent aromatic hydrocarbon group having 6 to 20 carbon atoms. $L^6$ represents an (n4+1)-valent aliphatic hydrocarbon group having 1 to 20 carbon atoms or an (n4+1)-valent aromatic hydrocarbon group having 6 to 20 carbon atoms. $L^7$ represents an aliphatic hydrocarbon chain having 2 to 6 carbon atoms.

<3> The resin composition for an acoustic matching layer according to <1> or <2> further includes a polyamine compound (B2), and the polyamine compound (B2) is a polyamine compound not having an oxygen atom as a constituent atom.

<4> In the resin composition for an acoustic matching layer according to <3>, the polyamine compound (B2) is a polyamine compound having an alicyclic ring.

<5> In the resin composition for an acoustic matching layer according to any one of <1> to <4>, the metal particles (C) include a metal atom in groups 4 to 12.

<6> In the resin composition for an acoustic matching layer according to any one of <1> to <5>, the metal particles (C) include at least one of Zn, Au, Ag, Zr, W, Ta, Fe, Cu, Ni, Pt, or Mo.

<7> In the resin composition for an acoustic matching layer according to any one of <1> to <6>, the equivalent ratio of contents of the epoxy resin (A) and the polyamine compound (B1) satisfies polyamine compound (B1)/epoxy resin (A)=0.5/1 to 1/0.5.

<8> In the resin composition for an acoustic matching layer according to <3> or <4>, the equivalent ratio of contents of the epoxy resin (A) and the polyamine compound (B2) satisfies polyamine compound (B2)/epoxy resin (A) 0.9.

<9> A cured product is formed by curing the resin composition for an acoustic matching layer according to any one of <1> to <8>.

<10> An acoustic matching sheet includes the cured product according to <9>.

<11> An acoustic probe includes the acoustic matching sheet according to <10> as an acoustic matching layer.

<12> An acoustic measuring apparatus includes the acoustic probe according to <11>.

<13> In the acoustic measuring apparatus according to <12>, the acoustic measuring apparatus is an ultrasound diagnostic apparatus.

<14> A method for producing an acoustic probe includes forming an acoustic matching layer by using the resin composition for an acoustic matching layer according to any one of <1> to <8>.

<15> An acoustic matching layer material set includes a base resin made of a resin composition including metal particles (C) and at least one epoxy resin (A) selected from the group consisting of bisphenol A epoxy resins, bisphenol F epoxy resins, and phenol novolac epoxy resins, and a curing agent including at least one polyamine compound (B1) represented by general formula (I) below.

   General formula (I)

In general formula (I), n represents an integer of 2 to 20. L represents an n-valent aliphatic hydrocarbon group having an aliphatic hydrocarbon chain into which at least one oxygen atom is incorporated or an n-valent group having an aromatic ring and an aliphatic hydrocarbon group having at least one oxygen atom.

In the description of the present invention, the expression "to" is meant to include the numerical values before and after "to" as the lower and upper limits.

In the description of the present invention, when the number of carbon atoms of a group is specified, the number of carbon atoms means the number of carbon atoms of the whole group. That is, when the group further has a substituent, the number of carbon atoms means the number of carbon atoms of the whole including the substituent.

In the description of the present invention, when there are a plurality of substituents, a plurality of linking groups, or the like represented by a particular symbol (hereinafter referred to as "substituents or the like") or when a plurality of substituents or the like are simultaneously or alternatively specified, the substituents or the like may be the same or different. Furthermore, even if not specifically stated, when a plurality of substituents or the like are adjacent to each other, they may be linked or fused to each other to form a ring.

The resin composition for an acoustic matching layer and the acoustic matching layer material set according to the present invention, when formed or processed into a desired sheet shape, can provide an acoustic matching sheet having high mechanical strength and little variation in intrasheet acoustic characteristics.

The acoustic matching sheet according to the present invention has high mechanical strength and little variation in intrasheet acoustic characteristics. The cured product according to the present invention is suitable as a constituent material of the acoustic matching layer according to the present invention.

The acoustic probe according to the present invention and the acoustic measuring apparatus including the acoustic probe each have high mechanical strength and little variation in acoustic characteristics.

The method for producing an acoustic probe according to the present invention can provide an acoustic probe having high mechanical strength and little variation in acoustic characteristics.

BRIEF DESCRIPTION OF THE DRAWINGS

FIG. 1 is a perspective view of an example of a convex ultrasound probe, which is one aspect of an acoustic probe.

DESCRIPTION OF THE PREFERRED EMBODIMENTS

Resin Composition for Acoustic Matching Layer

A resin composition for an acoustic matching layer according to the present invention (hereinafter also referred to simply as "a composition according to the present invention") includes an epoxy resin (A), a polyamine compound (B1), and metal particles (C). The epoxy resin (A) and the polyamine compound (B1) included in the composition according to the present invention fill gaps between the metal particles (C) and function as dispersion media for the metal particles (C).

Since the composition according to the present invention has the above configuration, an acoustic matching sheet formed from the composition has high mechanical strength and little variation in intrasheet acoustic characteristics. Although not clear, the reasons for this are presumably as follows.

In the composition according to the present invention, the polyamine compound (B1) has an aliphatic hydrocarbon group having at least one oxygen atom. Probably, the aliphatic hydrocarbon group interacts with the metal particles (C) to stabilize the state of dispersion of the metal particles (C) in the composition, whereby the metal particles (C) are very evenly distributed in an acoustic matching sheet.

When a polyamine compound not having an aliphatic hydrocarbon group having at least one oxygen atom is used alone, the rate of cure of the epoxy resin (A) in the presence of the epoxy resin (A) and the metal particles (C) is often considerably high or considerably low. When the rate of cure is considerably high, the epoxy resin (A) cures before the metal particles (C) are dispersed. On the other hand, when the rate of cure is considerably low, the epoxy resin (A) cures after the metal particles (C) sink. Thus, when a polyamine compound not having an aliphatic hydrocarbon group having at least one oxygen atom is used alone, a uniform sheet cannot be formed, leading to variation in acoustic characteristics. By contrast, the polyamine compound (B1) has characteristics between the above characteristics (adjusts the rate of cure) in the presence of the epoxy resin (A) and the metal particles (C) and thus allows the epoxy resin (A) to cure with the metal particles (C) being moderately dispersed. The composition according to the present invention produces both the above effects probably because of a combination of the dispersion stability of the metal particles (C) in the composition and the moderate rate of cure in forming a sheet.

Epoxy Resin (A)

The epoxy resin (A) used in the present invention includes at least one epoxy resin selected from the group consisting of bisphenol A epoxy resins, bisphenol F epoxy resins, and phenol novolac epoxy resins.

The bisphenol A epoxy resin used in the present invention is not particularly limited and may be any bisphenol A epoxy resin commonly used as a base resin of an epoxy adhesive. Specific examples of preferred bisphenol A epoxy resins include bisphenol A diglycidyl ethers (jER825, jER828, and jER834 (trade names), manufactured by Mitsubishi Chemical Corporation) and bisphenol A propoxylate diglycidyl ethers (manufactured by Sigma-Aldrich).

The bisphenol F epoxy resin used in the present invention is not particularly limited and may be any bisphenol F epoxy resin commonly used as a base resin of an epoxy adhesive. Specific examples of preferred bisphenol F epoxy resins include bisphenol F diglycidyl ethers (trade name: EPICLON830, manufactured by DIC Corporation) and 4,4'-methylenebis(N,N-diglycidylaniline).

The phenol novolac epoxy resin used in the present invention is not particularly limited and may be any phenol novolac epoxy resin commonly used as a base resin of an epoxy adhesive. Such a phenol novolac epoxy resin is marketed, for example, by Sigma-Aldrich under the product number 406775.

The epoxy resin (A) may be composed of at least one of the above epoxy resins or may include, in addition to at least one of the above epoxy resins, another epoxy resin (e.g., an aliphatic epoxy resin) as long as the effects of the present invention are not impaired. The content of the above three types of epoxy resins (the total content of a bisphenol A epoxy resin, a bisphenol F epoxy resin, and a phenol novolac epoxy resin) in the epoxy resin (A) is preferably 80 mass % or more, more preferably 90 mass % or more.

Polyamine Compound (B1)

The polyamine compound (B1) used in the present invention is a curing component that acts on the epoxy resin (A) to cure it and is represented by general formula (I) below.

            General formula (I)

In general formula (I), n represents an integer of 2 to 20 (preferably 3 to 20). L represents an n-valent aliphatic hydrocarbon group having an aliphatic hydrocarbon chain into which at least one oxygen atom is incorporated or an n-valent group having an aromatic ring and an aliphatic hydrocarbon group having at least one oxygen atom.

The polyamine compound (B1) is preferably at least one polyamine compound represented by general formula (II), (III), or (IV) below. This is because the dispersibility of the metal particles (C) can be further increased, and the rate of cure can be more readily adjusted to a desired rate not too fast and not too slow.

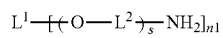            General formula (II)

In general formula (II), s represents an integer of 1 to 100, and n1 represents an integer of 2 to 20. $L^1$ represents an n1-valent aliphatic hydrocarbon group having 1 to 20 carbon atoms or an n1-valent aromatic hydrocarbon group having 6 to 20 carbon atoms, and $L^2$ represents an aliphatic hydrocarbon chain having 2 to 6 carbon atoms.

The above aliphatic hydrocarbon groups and aliphatic hydrocarbon chains may be linear or branched.

To provide an acoustic matching layer with further improved breaking energy and further reduced variation in acoustic characteristics, s is preferably an integer of 1 to 50, more preferably an integer of 2 to 20.

n1 is preferably an integer of 1 to 15, more preferably an integer of 2 to 6, still more preferably 3 or 4.

The above aliphatic hydrocarbon group represented by $L^1$ is preferably an n1-valent aliphatic hydrocarbon group having 2 to 15 carbon atoms, more preferably an n1-valent aliphatic hydrocarbon group having 3 to 10 carbon atoms, still more preferably an n1-valent aliphatic hydrocarbon group having 5 or 6 carbon atoms.

The above aromatic hydrocarbon group represented by $L^1$ is preferably an n1-valent aromatic hydrocarbon group having 6 to 15 carbon atoms, more preferably an n1-valent aromatic hydrocarbon group having 6 to 10 carbon atoms, still more preferably n1-valent benzene.

$L^2$ is more preferably an aliphatic hydrocarbon chain having 2 to 4 carbon atoms, still more preferably an aliphatic hydrocarbon chain having 2 or 3 carbon atoms.

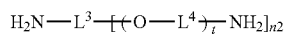            General formula (III)

In general formula (III), t represents an integer of 1 to 100, and n2 represents an integer of 1 to 19. $L^3$ represents an (n2+1)-valent aliphatic hydrocarbon group having 1 to 20 carbon atoms or an (n2+1)-valent aromatic hydrocarbon group having 6 to 20 carbon atoms, and $L^4$ represents an aliphatic hydrocarbon chain having 2 to 6 carbon atoms.

To provide an acoustic matching layer with further improved breaking energy and further reduced variation in acoustic characteristics, t is preferably an integer of 1 to 50, more preferably an integer of 2 to 20.

n2 is preferably an integer of 2 to 19, more preferably an integer of 2 to 5, still more preferably 3.

The above aliphatic hydrocarbon group represented by $L^3$ is preferably an (n2+1)-valent aliphatic hydrocarbon group having 2 to 10 carbon atoms, more preferably an (n2+1)-valent aliphatic hydrocarbon group having 2 to 6 carbon atoms, still more preferably an (n2+1)-valent aliphatic hydrocarbon group having 2 to 4 carbon atoms.

The above aromatic hydrocarbon group represented by $L^3$ is preferably an (n2+1)-valent aromatic hydrocarbon group having 6 to 15 carbon atoms, more preferably an (n2+1)-valent aromatic hydrocarbon group having 6 to 10 carbon atoms, still more preferably (n2+1)-valent benzene.

$L^4$ is more preferably an aliphatic hydrocarbon chain having 2 to 4 carbon atoms, still more preferably an aliphatic hydrocarbon chain having 2 or 3 carbon atoms.

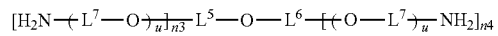            General formula (IV)

In general formula (IV), u represents an integer of 1 to 100, n3 and n4 each represent an integer of 1 or more, and the sum of n3 and n4 is 20 or less. $L^5$ represents an (n3+1)-valent aliphatic hydrocarbon group having 1 to 20 carbon atoms or an (n3+1)-valent aromatic hydrocarbon group having 6 to 20 carbon atoms. $L^6$ represents an (n4+1)-valent aliphatic hydrocarbon group having 1 to 20 carbon atoms or an (n4+1)-valent aromatic hydrocarbon group having 6 to 20 carbon atoms. $L^7$ represents an aliphatic hydrocarbon chain having 2 to 6 carbon atoms.

To provide an acoustic matching layer with further improved breaking energy and further reduced variation in acoustic characteristics, u is preferably an integer of 1 to 50, more preferably an integer of 2 to 20.

n3 and n4 are each preferably an integer of 2 to 10, more preferably an integer of 2 to 5, still more preferably 2 or 3.

The above aliphatic hydrocarbon group represented by $L^5$ is preferably an (n3+1)-valent aliphatic hydrocarbon group having 2 to 15 carbon atoms, more preferably an (n3+1)-valent aliphatic hydrocarbon group having 2 to 10 carbon atoms, still more preferably an (n3+1)-valent aliphatic hydrocarbon group having 3 to 6 carbon atoms.

The above aromatic hydrocarbon group represented by $L^5$ is preferably an (n3+1)-valent aromatic hydrocarbon group having 6 to 15 carbon atoms, more preferably an (n3+1)-valent aromatic hydrocarbon group having 6 to 10 carbon atoms, still more preferably (n3+1)-valent benzene.

The above aliphatic hydrocarbon group represented by $L^6$ is preferably an (n4+1)-valent aliphatic hydrocarbon group having 2 to 15 carbon atoms, more preferably an (n4+1)-valent aliphatic hydrocarbon group having 2 to 10 carbon atoms, still more preferably an (n4+1)-valent aliphatic hydrocarbon group having 3 to 6 carbon atoms.

The above aromatic hydrocarbon group represented by $L^6$ is preferably an (n4+1)-valent aromatic hydrocarbon group having 6 to 15 carbon atoms, more preferably an (n4+1)-valent aromatic hydrocarbon group having 6 to 10 carbon atoms, still more preferably (n4+1)-valent benzene.

$L^7$ is more preferably an aliphatic hydrocarbon chain having 2 to 4 carbon atoms, still more preferably an aliphatic hydrocarbon chain having 2 or 3 carbon atoms.

The polyamine compound (B1) used in the present invention may have one or more substituents T given below as long as the effects of the present invention are not impaired.

Examples of substituents T include the following.

Examples include alkyl groups (preferably having 1 to 20 carbon atoms), alkenyl groups (preferably having 2 to 20 carbon atoms), alkynyl groups (preferably having 2 to 20 carbon atoms), cycloalkyl groups (preferably having 3 to 20 carbon atoms, alkyl groups as used herein are generally meant to include cycloalkyl groups), aryl groups (preferably having 6 to 26 carbon atoms), aralkyl groups (preferably having 7 to 23 carbon atoms), heterocyclic groups (preferably heterocyclic groups having 2 to 20 carbon atoms, preferably 5- or 6-membered heterocyclic groups having at least one oxygen atom, sulfur atom, or nitrogen atom), alkoxy groups (preferably having 1 to 20 carbon atoms), aryloxy groups (preferably having 6 to 26 carbon atoms, alkoxy groups as used herein are generally meant to include aryloxy groups), alkoxycarbonyl groups (preferably having 2 to 20 carbon atoms), aryloxycarbonyl groups (preferably having 6 to 26 carbon atoms), amino groups (preferably amino groups having 0 to 20 carbon atoms, including alkylamino groups and arylamino groups), sulfamoyl groups (preferably having 0 to 20 carbon atoms), acyl groups (preferably having 1 to 20 carbon atoms), aryloyl groups (preferably having 7 to 23 carbon atoms, acyl groups as used herein are generally meant to include aryloyl groups), acyloxy groups (preferably having 1 to 20 carbon atoms), aryloyloxy groups (preferably having 7 to 23 carbon atoms, acyloxy groups as used herein are generally meant to include aryloyloxy groups), carbamoyl groups (preferably having 1 to 20 carbon atoms), acylamino groups (preferably having 1 to 20 carbon atoms), alkylthio groups (preferably having 1 to 20 carbon atoms), arylthio groups (preferably having 6 to 26 carbon atoms), alkylsulfonyl groups (preferably having 1 to 20 carbon atoms), arylsulfonyl groups (preferably having 6 to 22 carbon atoms), alkylsilyl groups (preferably having 1 to 20 carbon atoms), arylsilyl groups (preferably having 6 to 42 carbon atoms), alkoxysilyl groups (preferably having 1 to 20 carbon atoms), aryloxysilyl groups (preferably having 6 to 42 carbon atoms), phosphoryl groups (preferably phosphoryl groups having 0 to 20 carbon atoms, for example, —OP(=O)($R^P$)$_2$), phosphonyl groups (preferably phosphonyl groups having 0 to 20 carbon atoms, for example, —P(=O)($R^P$)$_2$), phosphinyl groups (preferably phosphinyl groups having 0 to 20 carbon atoms, for example, —P($R^P$)$_2$), (meth)acryloyl groups, (meth)acryloyloxy groups, (meth)acryloylimino groups ((meth)acrylamide groups), hydroxy groups, sulfanyl groups, carboxy groups, phosphate groups, phosphonate groups, sulfonate groups, cyano groups, and halogen atoms (e.g., fluorine, chlorine, bromine, and iodine). $R^P$ is a hydrogen atom, a hydroxy group, or a substituent (preferably a group selected from the group consisting of substituents T).

Each of these groups listed as substituents T may be further substituted with any of the above substituents T.

When a compound, a substituent, a linking group, or the like includes, for example, an alkyl group, an alkylene group, an alkenyl group, an alkenylene group, an alkynyl group, or an alkynylene group, these groups may be cyclic or chain-like, may be linear or branched, and may be substituted as described above or unsubstituted.

Specific examples of the polyamine compound (B1) used in the present invention include, but are not limited to, the following.

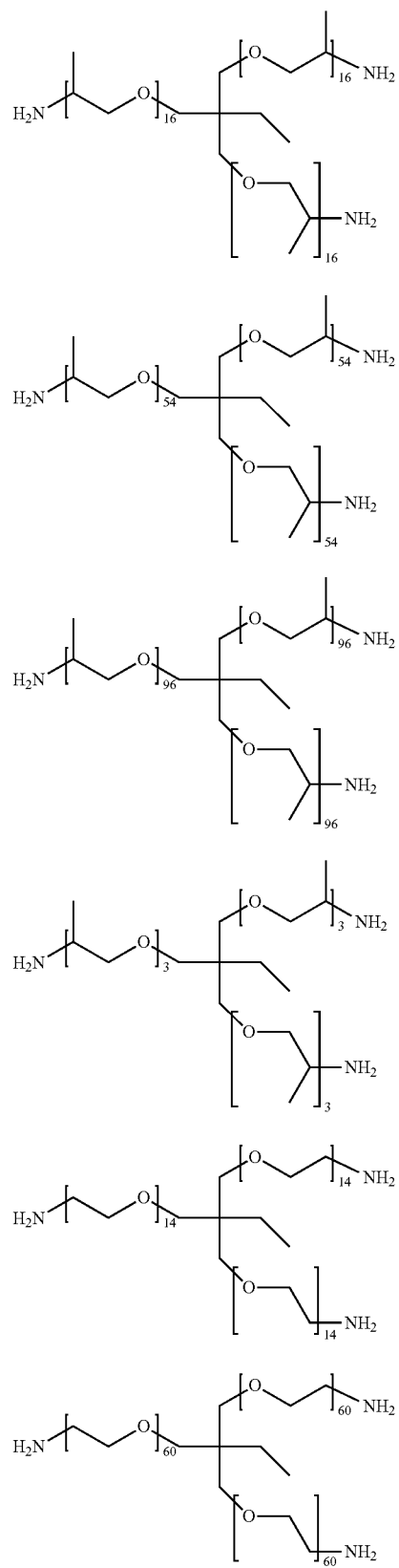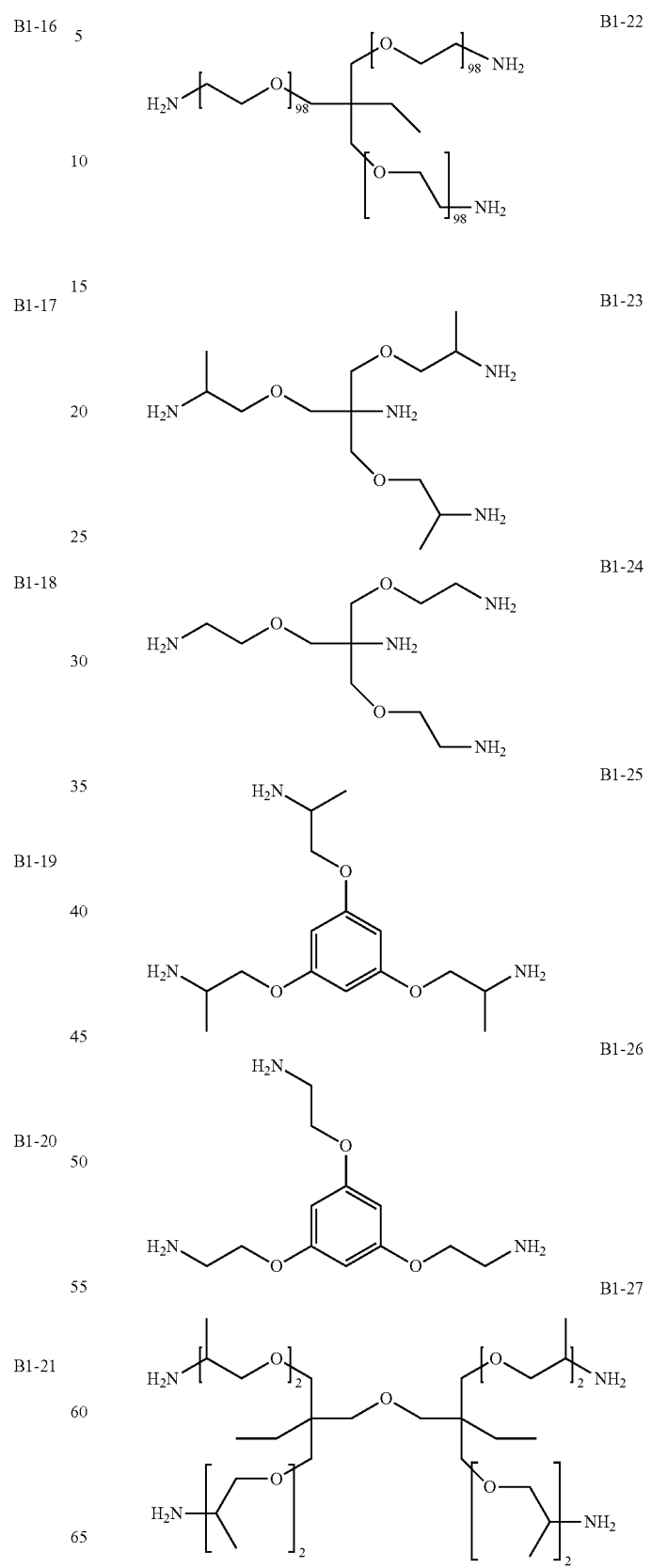

B1-28
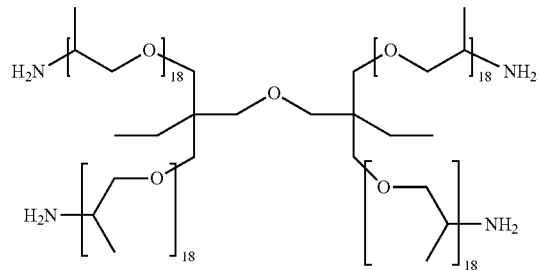
B1-29
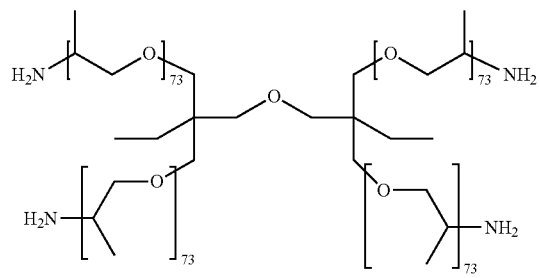
B1-30
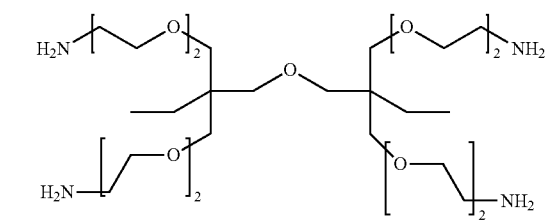
B1-31
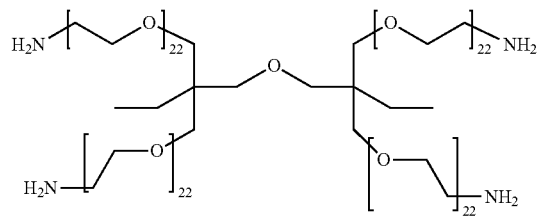
B1-32
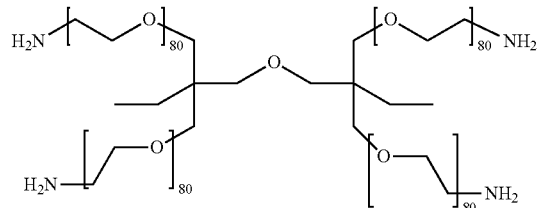
B1-33
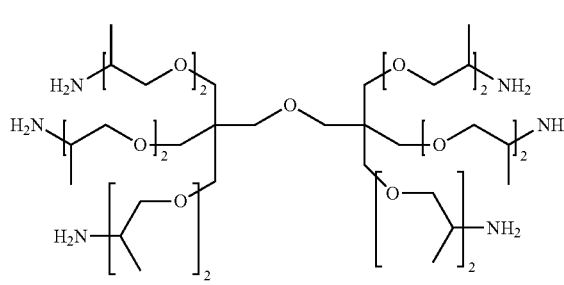
B1-34
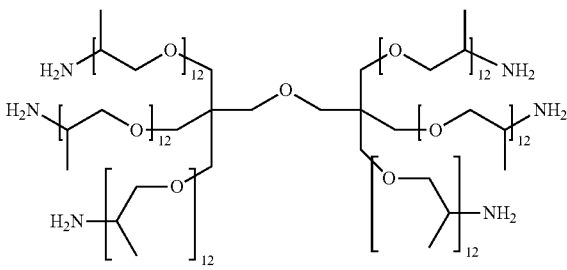
B1-35
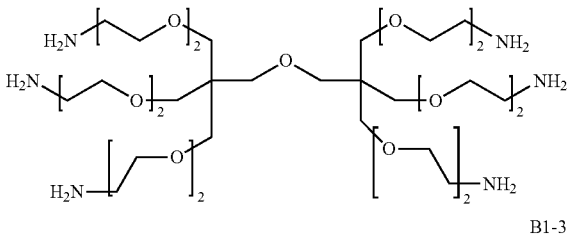
B1-36
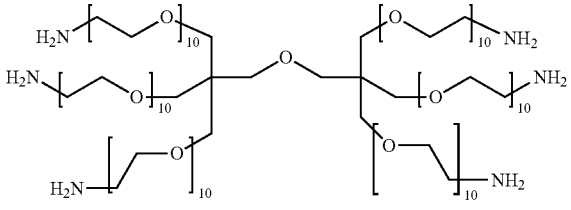
B1-37
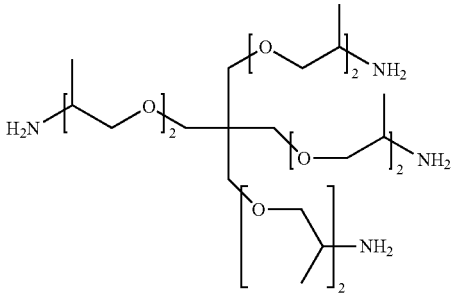
B1-38
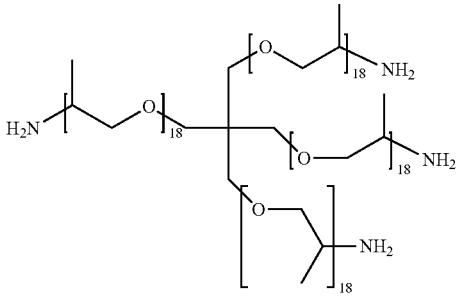
B1-39
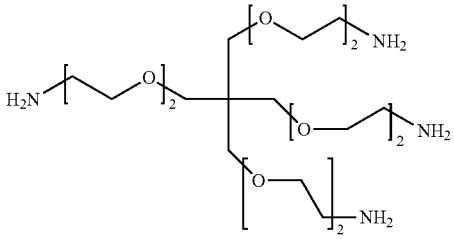

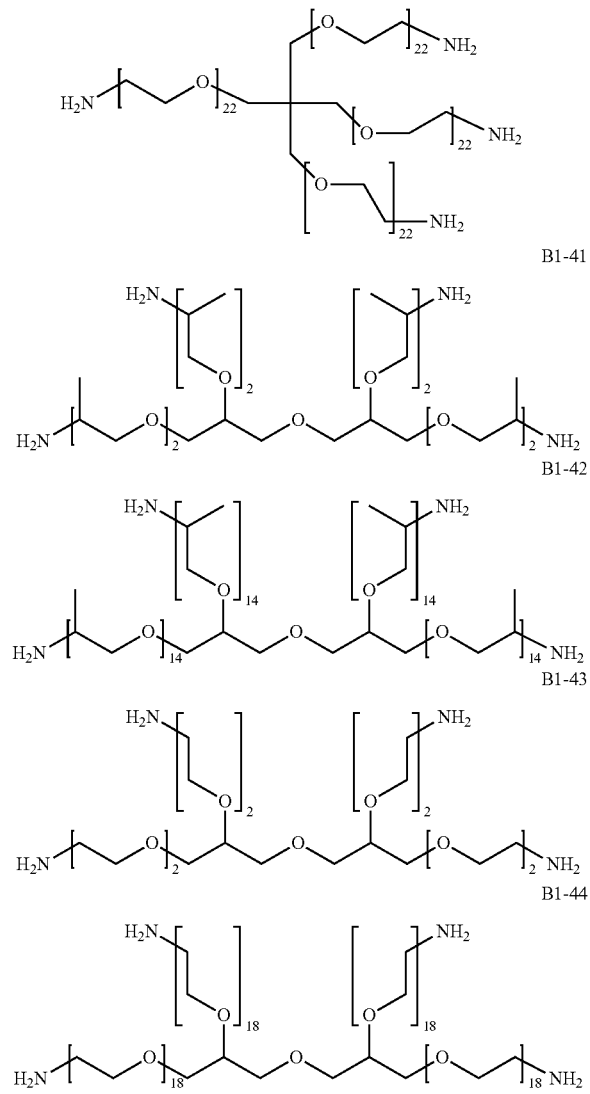

The polyamine compound (B1) may be composed of a single compound or a combination of two or more compounds. The polyamine compound (B1) used in the present invention can be synthesized by a usual method. Alternatively, a commercially available product may be used.

To improve the heat resistance and productivity of an acoustic matching layer, the composition according to the present invention preferably includes a polyamine compound (B2) not having an oxygen atom as a constituent atom.

The polyamine compound (B2) is not particularly limited except for not having an oxygen atom as a constituent atom, and is preferably a polyamine compound having an aromatic ring or an alicyclic ring, more preferably a polyamine compound having an alicyclic ring. The amino group in the polyamine compound (B2) is a primary amino group or a secondary amino group, preferably a primary amino group. The number of amino groups in the polyamine compound (B2) may be any number more than one, and is preferably 2 to 5, more preferably 2 to 4, still more preferably 2 or 3, further more preferably 2.

The polyamine compound (B2) having two primary amino groups is preferably a polyamine compound represented by general formula (V) below.

$$H_2N-L^8-NH_2 \qquad \text{General formula (V)}$$

$L^8$ represents a divalent linking group. The linking group does not have an oxygen atom.

$L^8$ is preferably an alkylene group, an arylene group, an imino group, or a divalent linking group formed by combining these groups.

The alkylene group may be linear or cyclic, or may be a combination of a linear alkylene group and a cyclic alkylene group. The number of carbon atoms in the alkylene group is preferably 1 to 30, more preferably 1 to 20. Specific examples of the alkylene group include methylene, ethylene, hexamethylene, 2,4,4-trimethylhexamethylene, 2,2,4-trimethylhexamethylene, 2-methylpentamethylene, cyclohexylene, dodecamethylene, and groups formed by combining at least two groups among them (preferably groups formed by combining two to five groups, more preferably groups formed by combining two to four groups, still more preferably groups formed by combining two or three groups).

The number of carbon atoms in the arylene group is preferably 6 to 14, more preferably 6 to 10, and specific examples include phenylene and naphthylene.

Examples of the divalent linking group formed by combining an alkylene group, an arylene group, or an imino group include groups formed by combining an alkylene group and an imino group and groups formed by combining an alkylene group and an arylene group.

$L^8$ is preferably a cyclic alkylene group, a group formed by combining a linear alkylene group and a cyclic alkylene group, an arylene group, or a group formed by combining a linear alkylene group and an arylene group, more preferably a cyclic alkylene group or a group formed by combining a linear alkylene group and a cyclic alkylene group.

The molecular weight of the polyamine compound (B2) is preferably 50 to 2000, more preferably 100 to 500.

Specific examples of the polyamine compound (B2) include polyethyleneamines (e.g., ethylenediamine (EDA), diethylenetriamine (DETA), triethylenetetramine (TETA), tetraethylenepentamine (TEPA), pentaethylenehexamine (PEHA)), dipropylenetriamine, polypropyleneamines (e.g., dipropylenetriamine), aminopropylated ethylenediamines (e.g., N-(3-aminopropyl)ethylenediamine, N,N'-bis(3-aminopropyl)ethylenediamine, N,N,N'-tris(3-aminopropyl)ethylenediamine), aminopropylated propylenediamines (e.g., N-(3-aminopropyl)propylenediamine, N,N'-bis(3-aminopropyl)propylenediamine, N,N,N'-tris(3-aminopropyl)propylenediamine), 1,6-hexanediamine (HMDA), 1,12-dodecanediamine, 2,2,4-trimethyl-1,6-hexanediamine, 2,4,4-trimethyl-1,6-hexanediamine, tripropylenetetramine, N,N'-bis(3-aminopropyl)-1,3-diaminopropane, N,N,N'-tris(3-aminopropyl)-1,3-diaminopropane, 2-methyl-1,5-pentanediamine (2-methylpentamethylenediamine), 1,2-diaminocyclohexane, 1,3-diaminocyclohexane (1,3-cyclohexanediamine), 1,4-diaminocyclohexane, hydrogenated ortho-toluenediamine, hydrogenated meta-toluenediamine, 1,3-bis(aminomethyl)cyclohexane, isophoronediamine (IPDA, 5-amino-1,3,3-trimethylcyclohexanemethylamine), menthanediamine (1,8-p-menthanediamine, MDA), norbornanediamine, 4,4'-diamino-3,3'-dimethyldicyclohexylmethane (4,4'-methylenebis(2-methylcyclohexylamine), bis(4-aminocyclohexyl)methane, 1,3-bis(aminocyclohexyl)propane, 1-cyclohexylamino-3-aminopropane, m-phenylenediamine, 4,4'-diaminodiphenylmethane (DDM, 4,4'-methylenedianiline), 4,4'-ethylenedianiline (4,4'-diaminobibenzyl, 4,4'-diamino-1,2-diphenylethane), tri(aminoethyl)benzene, tri(aminobutyl)naphthalene, toluenediamine (2-methyl-p-phenylenediamine), and diethyltoluenediamine.

Of these, 1,6-hexanediamine, 1,12-dodecanediamine, 2,2,4-trimethyl-1,6-hexanediamine, 2,4,4-trimethyl-1,6-hexanediamine, 1,3-diaminocyclohexane, 2-methyl-1,5-pentanediamine, m-phenylenediamine, 4,4'-ethylenedianiline, 4,4'-diamino-3,3'-dimethyldicyclohexylmethane, isophoronediamine, and menthanediamine are preferred, and isophoronediamine and menthanediamine are more preferred.

The polyamine compound (B2) may be composed of a single compound or a combination of two or more compounds. The polyamine compound (B2) used in the present invention can be synthesized by a usual method. Alternatively, a commercially available product may be used.

In addition to the polyamine compounds (B1) and (B2), the composition according to the present invention may include another amine compound (e.g., a tertiary amine compound) as long as the effects of the present invention are not impaired. The total content of the polyamine compounds (B1) and (B2) in the polyamine compounds contained in the composition according to the present invention is preferably 80 mass % or more, more preferably 90 mass % or more, still more preferably 95 mass % or more.

In the composition according to the present invention, curing reaction of the epoxy resin (A) may proceed over time. Accordingly, the properties of the composition may change over time, thus being unstable. However, for example, if the composition is preserved at a temperature of −10° C. or lower, the composition can be brought into a state in which each component is stably maintained with no curing reaction occurring or with curing reaction sufficiently inhibited.

It is also preferred that a resin composition including the epoxy resin (A) and the metal particles (C) be used as a base resin and that the base resin and a curing agent including the polyamine compound (B1) be used in the form of an acoustic matching layer material set in which the base resin and the curing agent are separate from each other. In forming an acoustic matching layer, the base resin and the curing agent are mixed together to prepare the composition according to the present invention, and a layer is formed using the composition, whereby the acoustic matching layer can be formed. The curing agent preferably includes the polyamine compound (B2).

In the composition according to the present invention, the equivalent ratio of the polyamine compound (B1) to the epoxy resin (A) may be, for example, polyamine compound (B1)/epoxy resin (A) (moles of amino groups×2 (moles of active hydrogen)/moles of epoxy groups)=0.5/1 to 1/0.5.

When the composition according to the present invention is prepared by using the above acoustic matching layer material set and mixing the base resin and the curing agent together in forming a layer, the base resin and the curing agent are preferably mixed together such that the mass ratio of the polyamine compound (B1) to the epoxy resin (A) is 1/99 to 80/20, more preferably 10/90 to 60/40.

In the composition according to the present invention, the equivalent ratio of the polyamine compound (B2) to the epoxy resin (A) may be, for example, polyamine compound (B2)/epoxy resin (A) (moles of active hydrogen of amino groups/moles of epoxy groups) 0.9, preferably ≤0.50 from the viewpoint of productivity.

Metal Particles (C)

The composition according to the present invention contains the metal particles (C). By adjusting the content of the metal particles (C), the density of the composition can be adjusted, and the acoustic impedance of an acoustic matching layer to be obtained can be adjusted to a desired level. The metal particles (C) may be surface treated.

The surface treatment of the metal particles may be performed by any method, and commonly used surface treatment techniques may be used. Examples of treatment methods include oil treatments with hydrocarbon oil, ester oil, lanolin, and the like, silicone treatments with dimethylpolysiloxane, methylhydrogenpolysiloxane, methylphenylpolysiloxane, and the like, fluorine compound treatments with perfluoroalkyl group-containing esters, perfluoroalkylsilanes, perfluoropolyethers, perfluoroalkyl group-containing polymers, and the like, silane coupling agent treatments with 3-methacryloxypropyltrimethoxysilane, 3-glycidoxypropyltrimethoxysilane, and the like, titanate coupling agent treatments with isopropyltriisostearoyl titanate, isopropyltris (dioctylpyrophosphate) titanate, and the like, metallic soap treatments, amino acid treatments with acylglutamic acid and the like, lecithin treatments with hydrogenated egg yolk lecithin and the like, collagen treatments, polyethylene treatments, moisturizing treatments, inorganic compound treatments, and mechanochemical treatments.

There is no particular limitation on a metal constituting the metal particles (C). The metal may be a metal atom alone, a metal carbide, a metal nitride, a metal oxide, a metal boride, or an alloy. Examples of alloys include high-tensile steel (Fe—C), chromium molybdenum steel (Fe—Cr—Mo), manganese molybdenum steel (Fe—Mn-Mo), stainless steel (Fe—Ni—Cr), 42 alloys, Invar (Fe—Ni), permendur (Fe—Co), silicon steel (Fe—Si), red brass, tombac (Cu—Zn), German silver (Cu—Zn—Ni), bronze (Cu—Sn), cupronickel (Cu—Ni), shakudo (Cu—Au), constantan (Cu—Ni), duralumin (Al—Cu), Hastelloy (Ni—Mo—Cr—Fe), Monel (Ni—Cu), Inconel (Ni—Cr—Fe), nichrome (Ni—Cr), ferromanganese (Mn—Fe), and cemented carbide (WC/Co).

From the viewpoint of general versatility and the ease of surface modification, the metal atom constituting the metal particles (C) preferably includes at least one metal atom in groups 4 to 12 of the periodic table.

More preferably, the metal atom includes at least one of Zn, Au, Ag, Zr, W, Ta, Fe, Cu, Ni, Pt, or Mo.

From the viewpoint of dispersion stability and acoustic stability, the particle size of the metal particles (C) used in the present invention is preferably 0.01 to 100 μm, more preferably 1 to 10 μm. As used herein, the "particle size" of the metal particles (C) means an average primary particle size.

As used herein, the average primary particle size means a volume average particle size. The volume average particle size is determined as described below.

The metal particles (C) are added to methanol at a concentration of 0.5 mass %, and the mixture is sonicated for 10 minutes to disperse the metal particles (C). The particle size distribution of the metal particles (C) thus treated is measured using a laser diffraction/scattering particle size distribution analyzer (manufactured by Horiba, Ltd., trade name: LA950V2), and the measured volumetric median diameter is used as the volume average particle size. The median diameter corresponds to a particle size at 50% in the particle size distribution represented in cumulative form.

In the composition according to the present invention, the contents of the metal particles (C), the epoxy resin (A), and the polyamine compound (B1) are each appropriately adjusted depending on, for example, the desired acoustic impedance. For example, when the acoustic matching layer is formed of multiple layers, the content of the metal particles (C) in the composition used for the acoustic matching layer on the piezoelectric element side can be relatively high, and the content of the metal particles (C) in the composition used for the acoustic matching layer on the acoustic lens side can be relatively low. This can provide a gradient in acoustic impedance from the piezoelectric element side toward the acoustic lens side, thus further increasing the efficiency of propagation of acoustic waves.

The composition according to the present invention may be composed of the epoxy resin (A), the polyamine compound (B1), the metal particles (C), and optionally the polyamine compound (B2). The composition may also contain other component as long as the effects of the present invention are not impaired. As the component other than epoxy resin (A), the polyamine compound (B1), the metal particles (C), and the polyamine compound (B2), for example, a curing retarder, a solvent, a dispersant, a pigment, a dye, an antistatic agent, an antioxidant, a flame retardant, or a thermal conductivity improver can be appropriately added.

In the composition according to the present invention, the sum of the contents of the epoxy resin (A), the polyamine compound (B1), and the metal particles (C) is preferably 80 mass % or more, more preferably 90 mass % or more. In the composition according to the present invention, the sum of the contents of the epoxy resin (A), the polyamine compound (B1), the metal particles (C), and the polyamine compound (B2) is preferably 80 mass % or more, more preferably 90 mass % or more, still more preferably 95 mass % or more. Preparation of resin composition for acoustic matching layer The resin composition for an acoustic matching layer according to the present invention can be obtained, for example, by kneading the components of the resin composition for an acoustic matching layer with a kneader, a pressure kneader, a Banbury mixer (continuous kneader), a two-roll kneading apparatus, or the like. This can provide a resin composition for an acoustic matching layer, the resin composition including an epoxy resin (A), a polyamine compound (B1), and metal particles (C) dispersed therein, preferably an epoxy resin (A), a polyamine compound (B1), a polyamine compound (B2), and metal particles (C) dispersed therein.

When an acoustic matching layer material set that includes a base resin made of a resin composition including an epoxy resin (A) and metal particles (C) and includes a curing agent including a polyamine compound (B1) is provided, the base resin can be obtained by kneading the epoxy resin (A) and the metal particles (C). The curing agent preferably includes a polyamine compound (B2). When an acoustic matching layer is produced, the base resin and the curing agent are mixed together to obtain the composition according to the present invention. The composition is cured while being shaped, whereby the acoustic matching layer or a precursor sheet thereof can be formed.

The kneading and shaping are preferably performed while removing bubbles, and thus usually performed under reduced pressure.

Acoustic Matching Sheet (Acoustic Matching Layer)

By forming the composition according to the present invention into a sheet shape and optionally, for example, cutting or dicing the sheet to a desired thickness or shape, an acoustic matching sheet can be obtained. The acoustic matching sheet is used as an acoustic matching layer of an acoustic probe. The configuration of an acoustic probe including an acoustic matching layer will be described later.

In producing the sheet, the composition is formed into a desired sheet shape at a low temperature at which no curing reaction occurs or curing proceeds slowly, and then the shaped product is cured, for example, by heating if necessary, to provide an acoustic matching sheet or a precursor sheet thereof. That is, the acoustic matching sheet according to the present invention is a cured product having a three-dimensional network structure formed by curing the composition according to the present invention.

Acoustic Probe

An acoustic probe according to the present invention has, as an acoustic matching layer, an acoustic matching sheet formed by using the composition according to the present invention.

An exemplary configuration of the acoustic probe according to the present invention is shown in FIG. 1. The acoustic probe shown in FIG. 1 is an ultrasound probe of an ultrasound diagnostic apparatus. An ultrasound probe uses, particularly, ultrasonic waves as acoustic waves for an acoustic probe. Thus, the basic structure of an ultrasound probe can be applied to an acoustic probe without any change.

Ultrasound Probe

An ultrasound probe 10, which is a main component part of an ultrasound diagnostic apparatus, has a function to generate ultrasonic waves as well as to transmit and receive ultrasonic beams. The ultrasound probe 10 has a configuration in which an acoustic lens 1, an acoustic matching layer 2, a piezoelectric element layer 3, and a backing member 4 are disposed in this order from a distal end (a surface to be in contact with a living body, or a subject) portion, as shown in FIG. 1. In recent years, ultrasound probes have also been proposed in which, for the purpose of receiving a high-order harmonic, a transmitting ultrasonic transducer (piezoelectric element) and a receiving ultrasonic transducer (piezoelectric element) are made of different materials to form a multilayer structure.

Piezoelectric Element Layer

The piezoelectric element layer 3 is a portion that generates ultrasonic waves, and electrodes are affixed to opposite sides of a piezoelectric element. When a voltage is applied, the piezoelectric element oscillates by repeating expansion and contraction to thereby generate ultrasonic waves.

As materials constituting piezoelectric elements, what is called ceramic inorganic piezoelectric bodies, which are obtained by polarizing single crystals of quartz, $LiNbO_3$, $LiTaO_3$, $KNbO_3$, and the like, thin films of ZnO, AlN, and the like, and $PbO_3$ ($ZrO_3$, $TiO_3$) sintered bodies, are widely used. In general, piezoelectric ceramics with high conversion efficiency, such as lead zirconate titanate (PZT), are used.

A piezoelectric element for detecting received waves on the high-frequency side is required to have sensitivity over a wider bandwidth. Thus, as a piezoelectric element suitable for a high frequency and a wide band, an organic piezoelectric body obtained using an organic macromolecular substance such as polyvinylidene fluoride (PVDF) is used.

Furthermore, for example, JP2011-071842A discloses a capacitive micromachined ultrasonic transducer (cMUT) that exhibits excellent short-pulse characteristics and wide-band characteristics, is suitable for mass production, provides an array structure with little variation in characteristics, and is obtained by using micro electro mechanical systems (MEMS).

In the present invention, any of the piezoelectric element materials can be preferably used.

Backing Member

The backing member 4, which is disposed in the back of the piezoelectric element layer 3, suppresses an excessive oscillation to shorten the pulse width of ultrasonic waves, thus contributing to improving the axial resolution in an ultrasound diagnostic image.

Acoustic Matching Layer

The acoustic matching layer 2 is disposed in order to achieve efficient transmission and reception of ultrasonic waves by reducing the difference in acoustic impedance between the piezoelectric element layer 3 and a subject.

Acoustic Lens

The acoustic lens 1 is disposed in order to converge ultrasonic waves in a slice direction by utilizing refraction to improve resolving power. The acoustic lens 1 comes into close contact with a living body, or a subject, and is required to match ultrasonic waves to the acoustic impedance of the living body (in the case of a human body, 1.4 to $1.7 \times 10^6$ $kg/m^2/sec$), and the amount of ultrasonic wave attenuation in the acoustic lens 1 itself is required to be small.

That is, by using, as a material for the acoustic lens 1, such a material that the sound velocity in the material is sufficiently lower than the sound velocity in a human body and that causes less ultrasonic wave attenuation and has an acoustic impedance value close to that of human body skin, the sensitivity to transmit and receive ultrasonic waves are increased.

The operation of the ultrasound probe 10 having such a configuration will be described. A voltage is applied to the electrodes disposed on the opposite sides of the piezoelectric element to resonate the piezoelectric element layer 3, thus transmitting an ultrasonic signal from the acoustic lens to a subject. At the time of reception, the piezoelectric element layer 3 is oscillated by a reflected signal (echo signal) from the subject, and the oscillation is electrically converted into a signal to obtain an image.

Method for Producing Acoustic Probe

The acoustic probe according to the present invention can be produced by a usual method provided that the resin composition for an acoustic matching layer according to the present invention is used. That is, a method for producing an acoustic probe according to the present invention includes forming an acoustic matching layer on a piezoelectric element by using the resin composition for an acoustic matching layer according to the present invention. The piezoelectric element can be provided on a backing member by a usual method.

Furthermore, an acoustic lens is formed on the acoustic matching layer by a usual method using a material for forming the acoustic lens.

Acoustic Measuring Apparatus

An acoustic measuring apparatus according to the present invention has the acoustic probe according to the present invention. The acoustic measuring apparatus has functions, for example, to display the signal strength of a signal received by the acoustic probe and to translate the signal into an image.

The acoustic measuring apparatus according to the present invention may be an ultrasonic measuring apparatus including an ultrasound probe.

Examples

The present invention will now be described in more detail with reference to examples in which ultrasonic waves are used as acoustic waves. It should be noted that in the present invention, not only ultrasonic waves but also any acoustic waves of audio frequencies may be used as long as appropriate frequencies are selected according to the subject, the measurement conditions, and so on. In the following examples, room temperature means 25° C.

Preparation of Resin Composition for Acoustic Matching Layer (Example 1)

One hundred parts by mass of metal particles (iron powder (Fe) (EW-I (trade name) manufactured by BASF) and 15 parts by mass of an epoxy resin (A-1) (bisphenol A diglycidyl ether ("jER825" (trade name) manufactured by Mitsubishi Chemical Corporation, epoxy equivalent weight: 170)) serving as a base resin were stirred for 4 minutes at 1800 rpm under a reduced pressure of 1.0 Pa at room temperature using a "THINKY MIXER ARV-310 (trade name, manufactured by THINKY CORPORATION)" while being defoamed. Thereafter, the resultant and 8 parts by mass of a polyamine compound (B-1) (polyoxyalkylene diamine D230 (trade name, manufactured by Mitsui Fine Chemicals, Inc., active hydrogen equivalent weight: 73) serving as a curing agent were stirred for 4 minutes at 1800 rpm under a reduced pressure of 1.0 Pa at room temperature using a "THINKY MIXER ARV-310 (trade name, manufactured by THINKY CORPORATION)" while being defoamed to prepare a resin composition for an acoustic matching layer (Example 1).

Resin compositions for acoustic matching layers of Examples other than Example 1 shown in Table 1 below were prepared in the same manner as the preparation of the resin composition for an acoustic matching layer of Example 1 except that compositions shown in Table 1 below were used.

The obtained resin compositions for acoustic matching layers were cured to produce sheets, and their breaking energy was measured. Acoustic impedances at five points in each sheet were measured, and their standard deviation was determined to evaluate variation in acoustic characteristics. A productivity test was performed using the resin compositions for acoustic matching layers, and a heat resistance test was performed using the sheets formed by curing the resin compositions for acoustic matching layers. Details of the tests will be described below.

Breaking Energy

The resin compositions for acoustic matching layers were each poured into a mold 5 cm long, 5 cm wide, and 0.4 mm high, and cured at 80° C. for 18 hours, then at 150° C. for 1 hour to produce sheets. The sheets were each punched to a length of 4 cm and a width of 5 mm to prepare tensile test specimens.

Using a tensile tester (Autograph AGS-X/20N) (trade name, manufactured by Shimadzu Corporation), the specimens were each stretched symmetrically in the longitudinal direction at a tensile speed of 30 mm/min to measure breaking energy. The criteria for evaluation are given below. In this test, A and B are acceptable.

Evaluation Criteria

A: 50 J or more
B: 45 J or more and less than 50 J
C: 40 J or more and less than 45 J
D: Less than 40 J Variation in Acoustic Impedance (AI)

The resin compositions for acoustic matching layers were each poured into a mold 5 cm long, 5 cm wide, and 2 mm high and cured at 80° C. for 18 hours, then at 150° C. for 1 hour to produce sheets. For five points, neighborhoods of four corners and the central part, of each sheet, acoustic impedances were each calculated from a product of a density and a sound velocity (density×sound velocity). The standard deviation of the acoustic impedances at the five points was determined, and the variation in acoustic characteristics was evaluated according to the following evaluation criteria.

Sound Velocity

The ultrasonic velocity was measured at 25° C. using a sing-around ultrasonic velocity measuring instrument (manufactured by Ultrasonic Engineering Co., Ltd., trade name "Model UVM-2") in accordance with JIS Z2353 (2003). At each of the five measurement sites, the whole inside of a circle with a diameter of 1.5 cm (a size of a single-channel small probe) was used as a measuring object.

Density

Densities at the five measurement sites at 25° C. were measured in accordance with a density measuring method of the A method (water displacement method) described in JIS K7112 (1999) by using an electronic densimeter (manufactured by Alfa Mirage Co., Ltd., trade name "SD-200L"). The density at each measurement site is defined as a density of a sheet specimen (10 mm×10 mm square) cut out from inside the above sound velocity measurement site (the circle with a diameter of 1.5 cm). The criteria for evaluation are given below. In this test, A and B are acceptable.

Evaluation Criteria

A: Less than 0.5
B: 0.5 or more and less than 0.7
C: 0.7 or more and less than 0.9
D: 0.9 or more Productivity Productivity was evaluated by determining the rate of cure of the resin compositions for acoustic matching layers on the basis of tackiness of the resin compositions for acoustic matching layers. The tackiness was determined by curing each resin composition for an acoustic matching layer in a thermostat chamber at 60° C. for a predetermined period of time and touching the surface of the resin composition for an acoustic matching layer to check if there was adhesion of the resin composition. The time until there was no adhesion of the resin composition for an acoustic matching layer (the time until the resin composition for an acoustic matching layer cured) was measured to thereby evaluate productivity.

Evaluation Criteria

A: 10 minutes or more and less than 20 minutes
B: 5 minutes or more and less than 10 minutes
C: 20 minutes or more and less than 30 minutes
D: 30 minutes or more
E: Less than 5 minutes From the viewpoint of productivity, an excessively short curing time is disadvantageous because curing is completed before the next step, and an excessively long curing time is also disadvantageous because it takes time. In this test, a curing time of 10 minutes or more and less than 20 minutes was defined to be optimal, and whether the productivity was high or low was evaluated as follows.

Productivity: A>B>C>D>E

Heat Resistance

Heat resistance was evaluated by using a glass transition temperature (Tg) of each cured product (the sheet obtained by curing each resin composition for an acoustic matching layer). The glass transition temperature (Tg) of each cured product was defined as a temperature at which the cured product exhibits a maximum value of tan δ in a dynamic viscoelastic measurement. The dynamic viscoelastic measurement was performed at a frequency of 1 Hz using a viscoelastometer (trade name: DMS6100) manufactured by Seiko Instruments Inc. The value of Tg was classified by the following evaluation criteria to evaluate heat resistance.

Evaluation Criteria

A: 140° C. or higher
B: 120° C. or higher and lower than 140° C.
C: 100° C. or higher and lower than 120° C.
D: 80° C. or higher and lower than 100° C.
E: Lower than 80° C.

TABLE 1

| | Epoxy resin (A) | | Polyamine compound (B1) | | | Polyamine compound (B2) | | | Metal particles (C) | | | | | | |
|---|---|---|---|---|---|---|---|---|---|---|---|---|---|---|---|
| | Type | Parts by mass | Type | Parts by mass | Equivalent ratio (1) | Type | Parts by mass | Equivalent ratio (2) | Type | Parts by mass | Specific gravity | Breaking energy | Variation in AI | Productivity | Heat resistance |
| Example 1 | A-1 | 15 | B1-1 | 5 | 1 | — | — | — | Fe | 100 | 3.4 | A | A | C | D |
| Example 2 | A-1 | 15 | B1-6 | 4 | 1 | — | — | — | Fe | 100 | 3.4 | B | A | C | E |
| Example 3 | A-1 | 15 | B1-11 | 9 | 1 | — | — | — | Fe | 100 | 3.3 | A | B | D | D |
| Example 4 | A-1 | 15 | B1-15 | 10 | 1 | — | — | — | Fe | 100 | 3.3 | A | A | D | D |
| Example 5 | A-1 | 15 | B1-19 | 8 | 1 | — | — | — | Fe | 100 | 3.3 | B | A | C | D |
| Example 6 | A-1 | 15 | B1-23 | 4 | 1 | — | — | — | Fe | 100 | 3.4 | A | B | D | D |
| Example 7 | A-1 | 15 | B1-24 | 4 | 1 | — | — | — | Fe | 100 | 3.4 | A | B | C | E |
| Example 8 | A-1 | 15 | B1-25 | 4 | 1 | — | — | — | Fe | 100 | 3.4 | A | B | D | C |
| Example 9 | A-1 | 15 | B1-26 | 4 | 1 | — | — | — | Fe | 100 | 3.4 | B | B | C | C |
| Example 10 | A-1 | 15 | B1-27 | 8 | 1 | — | — | — | Fe | 100 | 3.3 | A | B | D | D |
| Example 11 | A-1 | 15 | B1-30 | 7 | 1 | — | — | — | Fe | 100 | 3.3 | A | B | C | D |
| Example 12 | A-1 | 15 | B1-33 | 7 | 1 | — | — | — | Fe | 100 | 3.3 | A | B | D | D |
| Example 13 | A-1 | 15 | B1-35 | 6 | 1 | — | — | — | Fe | 100 | 3.3 | A | B | C | D |
| Example 14 | A-1 | 15 | B1-37 | 7 | 1 | — | — | — | Fe | 100 | 3.3 | A | B | D | D |
| Example 15 | A-1 | 15 | B1-39 | 6 | 1 | — | — | — | Fe | 100 | 3.3 | A | B | C | D |
| Example 16 | A-1 | 15 | B1-41 | 7 | 1 | — | — | — | Fe | 100 | 3.3 | A | B | D | D |
| Example 17 | A-1 | 15 | B1-43 | 6 | 1 | — | — | — | Fe | 100 | 3.3 | A | B | C | D |
| Example 18 | A-1 | 6 | B1-16 | 17 | 1 | — | — | — | Fe | 100 | 3.3 | A | A | D | E |
| Example 19 | A-1 | 3 | B1-17 | 20 | 1 | — | — | — | Fe | 100 | 3.3 | A | A | D | E |
| Example 20 | A-1 | 1 | B1-18 | 22 | 1 | — | — | — | Fe | 100 | 3.3 | B | B | D | E |
| Example 21 | A-2 | 15 | B1-15 | 9 | 1 | — | — | — | Fe | 100 | 3.3 | B | A | D | D |
| Example 22 | A-3 | 15 | B1-15 | 7 | 1 | — | — | — | Fe | 100 | 3.3 | B | A | D | D |
| Example 23 | A-4 | 15 | B1-15 | 10 | 1 | — | — | — | Fe | 100 | 3.2 | A | A | D | D |
| Example 24 | A-5 | 15 | B1-15 | 10 | 1 | — | — | — | Fe | 100 | 3.2 | A | A | D | D |
| Example 25 | A-6 | 15 | B1-15 | 7 | 1 | — | — | — | Fe | 100 | 3.3 | B | A | D | D |
| Example 26 | A-7 | 11 | B1-15 | 12 | 1 | — | — | — | Fe | 100 | 3.3 | A | A | D | D |
| Example 27 | A-1 | 15 | B1-15 | 10 | 1 | — | — | — | Zn | 100 | 3.2 | A | A | D | D |

TABLE 1-continued

|  | Epoxy resin (A) | | Polyamine compound (B1) | | | Polyamine compound (B2) | | | Metal particles (C) | | | | | | |
| --- | --- | --- | --- | --- | --- | --- | --- | --- | --- | --- | --- | --- | --- | --- | --- |
|  | Type | Parts by mass | Type | Parts by mass | Equivalent ratio (1) | Type | Parts by mass | Equivalent ratio (2) | Type | Parts by mass | Specific gravity | Breaking energy | Variation in AI | Productivity | Heat resistance |
| Example 28 | A-1 | 12 | B1-15 | 8 | 1 | — | — | — | Au | 100 | 3.6 | A | A | D | D |
| Example 29 | A-1 | 13 | B1-15 | 8 | 1 | — | — | — | Ag | 100 | 3.4 | A | A | D | D |
| Example 30 | A-1 | 15 | B1-15 | 10 | 1 | — | — | — | Zr | 100 | 3.2 | A | A | D | D |
| Example 31 | A-1 | 12 | B1-15 | 8 | 1 | — | — | — | Ta | 100 | 3.5 | A | A | D | D |

TABLE 2

|  | Epoxy resin (A) | | Polyamine compound (B1) | | | Polyamine compound (B2) | | | Metal particles (C) | | | | | | |
| --- | --- | --- | --- | --- | --- | --- | --- | --- | --- | --- | --- | --- | --- | --- | --- |
|  | Type | Parts by mass | Type | Parts by mass | Equivalent ratio (1) | Type | Parts by mass | Equivalent ratio (2) | Type | Parts by mass | Specific gravity | Breaking energy | Variation in AI | Productivity | Heat resistance |
| Example 32 | A-1 | 15 | B1-15 | 10 | 1 | — | — | — | Cu | 100 | 3.3 | A | A | D | D |
| Example 33 | A-1 | 15 | B1-15 | 10 | 1 | — | — | — | Ni | 100 | 3.3 | A | A | D | D |
| Example 34 | A-1 | 12 | B1-15 | 8 | 1 | — | — | — | Pt | 100 | 3.7 | A | A | D | D |
| Example 35 | A-1 | 15 | B1-15 | 10 | 1 | — | — | — | Mo | 100 | 3.4 | A | A | D | D |
| Example 36 | A-1 | 15 | B1-15 | 3 | 0.2 | — | — | — | Fe | 100 | 3.4 | B | A | D | D |
| Example 37 | A-1 | 15 | B1-15 | 5 | 0.5 | — | — | — | Fe | 100 | 3.4 | A | A | D | D |
| Example 38 | A-1 | 15 | B1-15 | 15 | 1.5 | — | — | — | Fe | 100 | 3.2 | A | A | D | D |
| Example 39 | A-1 | 15 | B1-15 | 22 | 2.1 | — | — | — | Fe | 100 | 3.2 | B | A | D | D |
| Example 40 | A-1 | 8 | B1-15 | 4 | 0.8 | — | — | — | Fe | 100 | 5.1 | A | A | D | D |
| Example 41 | A-1 | 30 | B1-15 | 15 | 0.8 | — | — | — | Fe | 100 | 2.9 | A | A | D | D |
| Example 42 | A-1 | 45 | B1-15 | 22 | 0.8 | — | — | — | Fe | 100 | 2.4 | A | A | D | D |
| Example 43 | A-1 | 60 | B1-15 | 30 | 0.8 | — | — | — | Fe | 100 | 2.2 | A | A | D | D |
| Example 44 | A-4 | 8 | B1-15 | 4 | 0.8 | — | — | — | Fe | 100 | 5.1 | A | A | D | D |
| Example 45 | A-4 | 30 | B1-15 | 15 | 0.8 | — | — | — | Fe | 100 | 2.9 | A | A | D | D |
| Example 46 | A-4 | 45 | B1-15 | 22 | 0.8 | — | — | — | Fe | 100 | 2.4 | A | A | D | D |
| Example 47 | A-4 | 60 | B1-15 | 30 | 0.8 | — | — | — | Fe | 100 | 2.2 | B | A | D | D |
| Example 48 | A-1 | 15 | B1-15 | 8 | 0.8 | B2-3 | 2 | 0.2 | Fe | 100 | 3.3 | B | A | A | B |
| Example 49 | A-1 | 15 | B1-15 | 6 | 0.5 | B2-3 | 4 | 0.5 | Fe | 100 | 3.3 | A | A | A | B |
| Example 50 | A-1 | 15 | B1-15 | 3 | 0.2 | B2-3 | 7 | 0.8 | Fe | 100 | 3.3 | A | A | B | A |
| Example 51 | A-1 | 15 | B1-15 | 8 | 0.8 | B2-6 | 2 | 0.2 | Fe | 100 | 3.3 | B | A | A | B |
| Example 52 | A-1 | 15 | B1-15 | 6 | 0.5 | B2-6 | 4 | 0.5 | Fe | 100 | 3.3 | A | A | A | B |
| Example 53 | A-1 | 15 | B1-15 | 3 | 0.2 | B2-6 | 7 | 0.8 | Fe | 100 | 3.3 | A | A | B | A |
| Example 54 | A-1 | 15 | B1-15 | 8 | 0.8 | B2-8 | 2 | 0.2 | Fe | 100 | 3.3 | A | A | A | B |
| Example 55 | A-1 | 15 | B1-15 | 6 | 0.5 | B2-8 | 4 | 0.5 | Fe | 100 | 3.3 | A | A | A | A |
| Example 56 | A-1 | 15 | B1-15 | 3 | 0.2 | B2-8 | 7 | 0.8 | Fe | 100 | 3.3 | A | A | B | A |
| Example 57 | A-1 | 15 | B1-15 | 8 | 0.8 | B2-9 | 2 | 0.2 | Fe | 100 | 3.4 | A | A | A | B |
| Example 58 | A-1 | 15 | B1-15 | 6 | 0.5 | B2-9 | 4 | 0.5 | Fe | 100 | 3.4 | A | A | A | A |
| Example 59 | A-1 | 15 | B1-15 | 3 | 0.2 | B2-9 | 7 | 0.8 | Fe | 100 | 3.4 | A | A | B | A |
| Example 60 | A-1 | 15 | B1-15 | 8 | 0.8 | B2-10 | 2 | 0.2 | Fe | 100 | 3.4 | A | A | A | B |
| Example 61 | A-1 | 15 | B1-15 | 6 | 0.5 | B2-10 | 4 | 0.5 | Fe | 100 | 3.4 | A | A | A | A |
| Example 62 | A-1 | 15 | B1-15 | 3 | 0.2 | B2-10 | 7 | 0.8 | Fe | 100 | 3.4 | A | A | B | A |

TABLE 3

|  | Epoxy resin (A) | | Polyamine compound (B1) | | | Polyamine compound (B2) | | | Metal particles (C) | | | | | | |
| --- | --- | --- | --- | --- | --- | --- | --- | --- | --- | --- | --- | --- | --- | --- | --- |
|  | Type | Parts by mass | Type | Parts by mass | Equivalent ratio (1) | Type | Parts by mass | Equivalent ratio (2) | Type | Parts by mass | Specific gravity | Breaking energy | Variation in AI | Productivity | Heat resistance |
| Comparative Example 1 | A-1 | 15 | — | — | — | B2-1 | 3 | 1 | Fe | 100 | 3.3 | C | D | E | D |
| Comparative Example 2 | A-1 | 15 | — | — | — | B2-2 | 4 | 1 | Fe | 100 | 3.3 | C | C | E | D |
| Comparative Example 3 | A-1 | 15 | — | — | — | B2-3 | 4 | 1 | Fe | 100 | 3.3 | C | C | E | D |
| Comparative Example 4 | A-1 | 15 | — | — | — | B2-4 | 3 | 1 | Fe | 100 | 3.3 | D | D | E | C |
| Comparative Example 5 | A-1 | 15 | — | — | — | B2-5 | 3 | 1 | Fe | 100 | 3.3 | D | D | E | D |
| Comparative Example 6 | A-1 | 15 | — | — | — | B2-6 | 2 | 1 | Fe | 100 | 3.3 | D | D | D | C |

TABLE 3-continued

|  | Epoxy resin (A) | | Polyamine compound (B1) | | | Polyamine compound (B2) | | | Metal particles (C) | | Specific gravity | Breaking energy | Variation in AI | Productivity | Heat resistance |
|---|---|---|---|---|---|---|---|---|---|---|---|---|---|---|---|
|  | Type | Parts by mass | Type | Parts by mass | Equivalent ratio (1) | Type | Parts by mass | Equivalent ratio (2) | Type | Parts by mass | | | | | |
| Comparative Example 7 | A-1 | 15 | — | — | — | B2-7 | 5 | 1 | Fe | 100 | 3.3 | C | C | E | C |
| Comparative Example 8 | A-1 | 15 | — | — | — | B2-8 | 5 | 1 | Fe | 100 | 3.3 | C | B | E | C |
| Comparative Example 9 | A-1 | 15 | — | — | — | B2-9 | 4 | 1 | Fe | 100 | 3.3 | C | B | E | C |
| Comparative Example 10 | A-1 | 15 | — | — | — | B2-10 | 4 | 1 | Fe | 100 | 3.3 | C | B | E | C |

NOTES OF TABLES

"–" means, for example, not containing the corresponding component.
Equivalent ratio (1): polyamine compound (B1)/epoxy resin (A)
Equivalent ratio (2): polyamine compound (B2)/epoxy resin (A)
Epoxy Compound (A)
(A-1) Bisphenol A diglycidyl ether ("jER825" (trade name) manufactured by Mitsubishi Chemical Corporation, epoxy equivalent weight: 170)
(A-2) Bisphenol A diglycidyl ether ("jER828" (trade name) manufactured by Mitsubishi Chemical Corporation, epoxy equivalent weight: 190)
(A-3) Bisphenol A diglycidyl ether ("jER834" (trade name) manufactured by Mitsubishi Chemical Corporation, epoxy equivalent weight: 230)
(A-4) Bisphenol F diglycidyl ether ("EPICLON830" (trade name) manufactured by DIC Corporation, epoxy equivalent weight: 170)
(A-5) Epoxy novolac resin (manufactured by Sigma-Aldrich, product number 406775, epoxy equivalent weight: 170)
(A-6) Bisphenol A propoxylate diglycidyl ether (manufactured by Sigma-Aldrich, epoxy equivalent weight: 228)
(A-7) 4,4'-Methylenebis(N,N-diglycidylaniline) (manufactured by Tokyo Chemical Industry Co., Ltd., epoxy equivalent weight: 106)

Polyamine Compound (B1)
Polyamine compounds used in EXAMPLES are exemplary compounds listed above.

Polyamine Compound (B2)
B2-1: 1,6-Hexanediamine (manufactured by Tokyo Chemical Industry Co., Ltd., active hydrogen equivalent weight: 29)
B2-2: 1,12-Dodecanediamine (manufactured by Tokyo Chemical Industry Co., Ltd., active hydrogen equivalent weight: 50)
B2-3: Trimethylhexamethylenediamine (manufactured by Tokyo Chemical Industry Co., Ltd., mixture of 2,2,4-trimethyl-1,6-hexanediamine and 2,4,4-trimethyl-1,6-hexanediamine, active hydrogen equivalent weight: 40)
B2-4: 1,3-Cyclohexanediamine (manufactured by Tokyo Chemical Industry Co., Ltd., active hydrogen equivalent weight: 29)
B2-5: 2-Methylpentamethylenediamine (manufactured by Tokyo Chemical Industry Co., Ltd., active hydrogen equivalent weight: 29)
B2-6: m-Phenylenediamine (manufactured by Tokyo Chemical Industry Co., Ltd., active hydrogen equivalent weight: 27)
B2-7: 4,4'-Ethylenedianiline (manufactured by Tokyo Chemical Industry Co., Ltd., active hydrogen equivalent weight: 53)
B2-8: 4,4'-Methylenebis(2-methylcyclohexylamine) (manufactured by Tokyo Chemical Industry Co., Ltd., active hydrogen equivalent weight: 59)
B2-9: 5-Amino-1,3,3-trimethylcyclohexanemethylamine (manufactured by FUJIFILM Wako Pure Chemical Corporation, active hydrogen equivalent weight: 43)
B2-10: 1,8-p-Menthanediamine (manufactured by Aldrich, active hydrogen equivalent weight: 43)

Metal Particles (C)
Fe: Iron powder (EW-I (trade name) manufactured by BASF, average particle size: 2 μm)
Zn: Zinc powder (average particle size: 3 μm)
Au: Gold powder (average particle size: 1 μm)
Ag: Silver powder (average particle size: 1 μm)
Zr: Zirconia powder (average particle size: 2 μm)
Ta: Tantalum powder (average particle size: 3 μm)
Cu: Copper powder (average particle size: 3 μm)
Ni: Nickel powder (average particle size: 2 μm)
Pt: Platinum powder (average particle size: 1 μm)
Mo: Molybdenum powder (Mo-3 manufactured by Japan New Metals Co., Ltd., average particle size: 3 μm)

Metal powders without company names were prepared by pulverization in our company.

As shown in Table 1 above, sheets formed by using compositions prepared by combining an epoxy resin (A), metal particles (C), and a diamine compound not satisfying the requirements of the present invention had poor mechanical strength and great variation in intrasheet acoustic characteristics (Comparative Examples 1 to 7).

By contrast, sheets formed by using compositions prepared by combining an epoxy resin (A), metal particles (C), and a polyamine compound (B1) had high mechanical strength and little variation in intrasheet acoustic characteristics (Examples 1 to 62).

While the present invention has been described in connection with embodiments thereof, we do not intend to limit our invention in any detail of the description unless otherwise specified. Rather, the invention should be broadly construed without departing from the spirit and scope of the invention as defined by the appended claims.

REFERENCE SIGNS LIST 1 acoustic lens
2 acoustic matching layer 3 piezoelectric element layer
4 backing member
7 housing
9 cord
10 ultrasound search unit (probe)

What is claimed is:

1. A resin composition for an acoustic matching layer, comprising:
an epoxy resin (A);
a polyamine compound (B1) represented by general formula (I) below; and
metal particles (C),
wherein the epoxy resin (A) includes at least one epoxy resin selected from the group consisting of bisphenol A epoxy resins, bisphenol F epoxy resins, and phenol novolac epoxy resins:

   General formula (I)

where, in general formula (I), n represents an integer of 2 to 20, and L represents an n-valent aliphatic hydrocarbon group having an aliphatic hydrocarbon chain into which at least one oxygen atom is incorporated or an n-valent group having an aromatic ring and an aliphatic hydrocarbon group having at least one oxygen atom,
wherein the metal particles (C) include at least one of Zn, Au, Zr, W, Ta, Fe, Cu, Ni, Pt, or Mo,
wherein the resin composition further comprises a polyamine compound (B2), and wherein the polyamine compound (B2) is a polyamine compound not having an oxygen atom as a constituent atom and is represented by general formula (V):

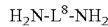   General formula (V)

wherein, in general formula (V), $L^8$ represents an alkylene group, an imino group, or a divalent linking group formed by combining these groups and
wherein an equivalent ratio of contents of the epoxy resin (A) and the polyamine compound (B1) satisfies polyamine compound (B1)/epoxy resin (A)=0.5/1 to 1/0.5.

2. The resin composition for an acoustic matching layer according to claim 1, wherein the polyamine compound (B1) is at least one polyamine compound represented by general formula (II), (III), or (IV) below:

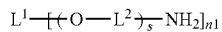   General formula (II)

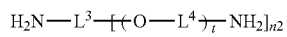   General formula (III)

   General formula (IV)

where, in general formula (II), s represents an integer of 1 to 100, n1 represents an integer of 2 to 20, $L^1$ represents an n1-valent aliphatic hydrocarbon group having 1 to 20 carbon atoms or an n1-valent aromatic hydrocarbon group having 6 to 20 carbon atoms, and $L^2$ represents an aliphatic hydrocarbon chain having 2 to 6 carbon atoms,
in general formula (III), t represents an integer of 1 to 100, n2 represents an integer of 1 to 19, $L^3$ represents an (n2+1)-valent aliphatic hydrocarbon group having 1 to 20 carbon atoms or an (n2+1)-valent aromatic hydrocarbon group having 6 to 20 carbon atoms, and $L^4$ represents an aliphatic hydrocarbon chain having 2 to 6 carbon atoms, and
in general formula (IV), u represents an integer of 1 to 100, n3 and n4 each represent an integer of 1 or more, a sum of n3 and n4 is 20 or less, $L^5$ represents an (n3+1)-valent aliphatic hydrocarbon group having 1 to 20 carbon atoms or an (n3+1)-valent aromatic hydrocarbon group having 6 to 20 carbon atoms, $L^6$ represents an (n4+1)-valent aliphatic hydrocarbon group having 1 to 20 carbon atoms or an (n4+1)-valent aromatic hydrocarbon group having 6 to 20 carbon atoms, and $L^7$ represents an aliphatic hydrocarbon chain having 2 to 6 carbon atoms.

3. The resin composition for an acoustic matching layer according to claim 1, wherein the polyamine compound (B2) is a polyamine compound having an alicyclic ring.

4. The resin composition for an acoustic matching layer according to claim 1, wherein an equivalent ratio of contents of the epoxy resin (A) and the polyamine compound (B2) satisfies polyamine compound (B2)/epoxy resin (A)≤0.9.

5. A cured product formed by curing the resin composition for an acoustic matching layer according to claim 1.

6. An acoustic matching sheet comprising the cured product according to claim 5.

7. An acoustic probe comprising the acoustic matching sheet according to claim 6 as an acoustic matching layer.

8. An acoustic measuring apparatus comprising the acoustic probe according to claim 7.

9. The acoustic measuring apparatus according to claim 8, wherein the acoustic measuring apparatus is an ultrasound diagnostic apparatus.

10. A method for producing an acoustic probe, comprising forming an acoustic matching layer from the resin composition for an acoustic matching layer according to claim 1.

11. An acoustic matching layer material set comprising:
a base resin made of a resin composition including metal particles (C) and at least one epoxy resin (A) selected from the group consisting of bisphenol A epoxy resins, bisphenol F epoxy resins, and phenol novolac epoxy resins; and
a curing agent including at least one polyamine compound (B1) represented by general formula (I) below:

   General formula (I)

where, in general formula (I), n represents an integer of 2 to 20, and L represents an n-valent aliphatic hydrocarbon group having an aliphatic hydrocarbon chain into which at least one oxygen atom is incorporated or an n-valent group having an aromatic ring and an aliphatic hydrocarbon group having at least one oxygen atom,
wherein the metal particles (C) include at least one of Zn, Au, Zr, W, Ta, Fe, Cu, Ni, Pt, or Mo,
wherein the curing agent further comprises a polyamine compound (B2), and wherein the polyamine compound (B2) is a polyamine compound not having an oxygen atom as a constituent atom and is represented by general formula (V):

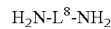   General formula (V)

wherein, in general formula (V), $L^8$ represents an alkylene group, an imino group, or a divalent linking group formed by combining these groups and
wherein an equivalent ratio of contents of the epoxy resin (A) and the polyamine compound (B1) satisfies polyamine compound (B1)/epoxy resin (A)=0.5/1 to 1/0.5.

* * * * *